US006838484B2

(12) United States Patent
Steiner et al.

(10) Patent No.: US 6,838,484 B2
(45) Date of Patent: Jan. 4, 2005

(54) FORMULATIONS COMPRISING SELECTIVE ANDROGEN RECEPTOR MODULATORS

(75) Inventors: Mitchell S. Steiner, Germantown, TN (US); Karen A. Veverka, Cordova, TN (US); James T. Dalton, Columbus, OH (US); Duane D. Miller, Germantown, TN (US); Yali He, Florence, SC (US); Donghua Yin, St. Louis, MO (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/270,232

(22) Filed: Oct. 15, 2002

(65) Prior Publication Data

US 2003/0162761 A1 Aug. 28, 2003

Related U.S. Application Data

(63) Continuation-in-part of application No. 09/935,044, filed on Aug. 23, 2001, now Pat. No. 6,492,554, and a continuation-in-part of application No. 09/935,045, filed on Aug. 23, 2001, now Pat. No. 6,569,896.
(60) Provisional application No. 60/367,355, filed on Aug. 24, 2000, and provisional application No. 60/300,083, filed on Jun. 25, 2001.

(51) Int. Cl.$^7$ ............................................. A61K 31/16
(52) U.S. Cl. .................. 514/616; 514/617; 514/697; 514/520; 514/602; 514/478; 514/415; 514/312
(58) Field of Search ................................ 514/616, 617, 514/597, 520, 602, 478, 415, 312; 564/153, 157, 158

(56) References Cited

U.S. PATENT DOCUMENTS

| | | | |
|---|---|---|---|
| 3,875,229 A | 4/1975 | Gold | |
| 4,139,638 A | 2/1979 | Neri et al. | |
| 4,191,775 A | 3/1980 | Glen | |
| 4,239,776 A | 12/1980 | Glen et al. | |
| 4,282,218 A | 8/1981 | Glen et al. | |
| 4,386,080 A | 5/1983 | Crossley et al. | |
| 4,465,507 A | 8/1984 | Konno et al. | |
| 4,636,505 A | 1/1987 | Tucker | |
| 4,880,839 A | 11/1989 | Tucker | |
| 5,162,504 A | 11/1992 | Horoszewicz | |
| 5,609,849 A | 3/1997 | Kung | |
| 5,656,651 A | 8/1997 | Sovak et al. | |
| 6,019,957 A | 2/2000 | Miller et al. | |
| 6,071,957 A | 6/2000 | Miller et al. | |
| 6,160,011 A | 12/2000 | Miller et al. | |
| 6,569,896 B2 * | 5/2003 | Dalton et al. | ................ 514/493 |
| 2001/0012839 A1 | 8/2001 | Miller et al. | |

FOREIGN PATENT DOCUMENTS

| | | |
|---|---|---|
| EP | 0 040 932 | 2/1981 |
| EP | 0 100 172 | 2/1984 |
| EP | 000 2892 | 2/1985 |
| EP | 0 253 503 * | 1/1988 |
| GB | 1360001 | 3/1970 |
| JP | 52-128329 | 10/1977 |
| JP | 54-63047 | 12/1980 |
| WO | WO 95/19770 | 7/1995 |
| WO | WO 95/19970 | 7/1995 |
| WO | WO 98 05962 | 2/1998 |
| WO | WO 98/53826 | 12/1998 |
| WO | WO 98/55153 | 12/1998 |
| WO | WO 01 27622 | 4/2001 |
| WO | WO 01 28990 | 4/2001 |
| WO | WO 01 34563 | 5/2001 |
| WO | WO 02 00617 | 1/2002 |
| WO | WO 02/016310 | 2/2002 |

OTHER PUBLICATIONS

U.S. Appl. No. 09/935,044, filed Aug. 23, 2001, Dalton et al.
U.S. Appl. No. 09/935,045, filed Aug. 23, 2001, Dalton et al.
U.S. Appl. No. 09/644,970, filed Aug. 23, 2001, Dalton et al.
Howard Tucker and Glynne J. Chesterson, J. Med Chem. 1988, 31, pp. 885–887, "Resolution of the Nonsteroidal Antiandrogen—4'–Cyano–3–[(4–fluorophenyl)sulfonyl]–2–hydroxy–2–methyl–3'–(trifluoromethyl)–propionamilide and the Determination of the Absolute Configuration of hte Active Enantiomer".
D. McKillop, et al., "Enantioselective metabolism and pharmacokinetics of Casodex in the male rat", Xenobiotica, 1995, vol. 25, No. 6, 623–634.

(List continued on next page.)

*Primary Examiner*—Shailendra Kumar
(74) *Attorney, Agent, or Firm*—Eitan, Pearl, Latzer & Cohen Zedek, LLP; Mark S. Cohen (57) ABSTRACT

The present invention relates to pharmaceutical compositions and formulations comprising a novel class of androgen receptor targeting agents (ARTA) which demonstrate androgenic and anabolic activity of a nonsteroidal ligand for the androgen receptor. The agents define a new subclass of compounds which are selective androgen receptor modulators (SARM) which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia,osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; and/or e) decreasing the incidence of, halting or causing a regression of prostate cancer. The present invention provides pharmaceutical compositions comprising the selective androgen receptor modulator compounds, together with pharmaceutically acceptable excipients.

85 Claims, 1 Drawing Sheet

OTHER PUBLICATIONS

Leonid Kirkovsky, et al., "[$^{125}$I]–Radionated Analogs as Potential Imaging Agents for Prostate Cancer", Poster Presentation MEDI 155, 214th ACS National Meeting, Las Vegas, NV, Sept. 7–11, 1997, Department of Pharmaceutical Sciences, University of Tennessee, Memphis, TN 38163.

David T. Baird and Anna F. Glasier, "Hormonal Contraception—Drug Therapy", The New England Journal of Medicine, May 27, 1993, pp. 1543–1549.

F.C. W. Wu, "Male Contraception: Current Status and Future Prospects", Clinical Endocrinology, (1988), 29, pp. 443–465.

Carl Djerassi and S.P. Leibo, "A new look at male contraception", Nature, vol. 370, pp. 11–12.

World Health Organisation Task Force on Methods for the Regulation of Male Fertility, "Contraceptive efficacy of testosterone–induced azoospermia in normal men", The Lancet, vol. 336, Oct. 20, 1990, pp. 955–959 and 1517–1518.

C. G. Francisco, et al., "Long–acting contraceptive agents: testosterone esters of unsaturated acids", Steroids, Jan. 1990, vol. 55, Butterworths.

John M. Hoberman and Charles E. Yesalis, "The History of Synthetic Testosterone", Scientific American, Feb. 1995, pp. 76–81.

Leonid Kirkovsky, et al., "Approaches to Irreversible non–steroidal chiral antiandrogens", Department of Pharmaceutical Sciences, University of Tennessee, 47th Southeast/51st Southwest Joint Regional Meeting of the American Chemical Society, Memphis, TN, Nov. 29–Dec. 1, 1995.

David J. Handelsman, "Bridging the gender gap in contraception: another hurdle cleared" The Medical Journal of Australia, vol. 154, Feb. 18, 1996, pp. 230–233.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4–(trifluoromethyl)–2H–pyranol[3,2–g]quinolin–2–one. Bioorg. Med. Chem. Lett., 9: 1003, 1999.

Zhi L., Tegley CM, Marschke KB, and Jones TK. Switching androgen receptor antagonists to agonists by modifying C–ring substitunets on piperidinol[3,2–g]quinolone. Bioorg. Med. Chem. Lett., 9: 1009, 1999.

Higuchi RI, Edwards JP, Caferro TR, Ringgenberg JD, Kong JW, Hamann LG, Arienti KL, Marschke KB, Davis RI, Farmer LI, and Jones TK. 4–Alkyl– and 3,4–diaklyl–1,2,3,4–tetrahydro–8–pyridonol[5,6–g]quinolines: potent, nonsteroidal androgen receptor agonists. Bioorg. Med. Chem. Lett., 9: 1335, 1999.

Hamann LG, Mani NS, Davis RL, Wang XN, Marschke KB, and Jones TK. Discovery of a potent, orally active nonsteroidal androgen receptor agonist: 4–ethyl–1,2,3,4–tetrahydro–6–(trifluoromethyl)–8–pyridomo[5,6–g]–quinoline (LG121071). J. Med. Chem. Lett., 42: 210, 1999.

Rosen J, Day A, Jones TK Jones ET, Nadzan AM, and Stein RB. Intracellular receptors and signal transducers and activators of transcription superfamilies: novel targets for small–molecule drug discovery. J. Med. Chem., 38: 4855, 1995.

Dalton JT, Mukherjee A, Zhu Z, Kirkovsky L, and Miller DD. Discovery of Nonsteroidal Androgens. Biochem. Biophys. Res. Commun.,244(1):1–4, 1998.

Edwards JP, West SJ, Pooley CLF, Marschke KB, Farmer LJ, Jones TK. New nonsteroidal androgen receptor modulators based on 4–(trifluoromethyl)–2–(1H)–Pyrololidino[3,2–g]quinolone. Bioorg. Med. Chem. Lett., 8: 745, 1998.

Eliason et al., "High Throughput Fluorescence Polarization–Based Screening Assays for the Identification of Novel Nuclear Receptors Ligands," Abstractsa of Papers, 223rd ACS National Meeting, Orlando, FL, United States, Apr. 7, 2002.

Berger et al., "Concepts and limitations in the application of radiolabeled antiandrogens, estrogens, or androgens as isotropic scanning agents for the prostate", Invest. Urol, (1975), 1391, 10–16.

* cited by examiner

Figure 1

FORMULATIONS COMPRISING SELECTIVE ANDROGEN RECEPTOR MODULATORS

CROSS REFERENCE TO RELATED APPLICATIONS

This application is a CIP of Ser. No. 09/935,044, Aug. 23, 2001 U.S. Pat. No. 6,492,554, and Ser. No. 09/935,045, Aug. 23, 2001 U.S. Pat. No. 6,569,896; which claims priority of Ser. No. 09/644,970, Aug. 24, 2000, which was converted to 60/367,355; and claims benefit of 60/300,083, Jun. 25, 2001.

GOVERNMENT INTEREST STATEMENT

This invention was made in whole or in part with government support under grant number R29 CA068096 awarded by the National Cancer Institute, National Institute of Health, and under grant number R15 HD35329, awarded by the National Institute of Child Health and Human Development, National Institute of Health. The government may have certain rights in the invention.

FIELD OF INVENTION

The present invention relates to pharmaceutical compositions and formulations comprising a novel class of androgen receptor targeting agents (ARTA), which demonstrate androgenic and anabolic activity of a nonsteroidal ligand for the androgen receptor. The agents define a new subclass of compounds, which are selective androgen receptor modulators (SARMs) useful for a) male contraception; b) treatment of a variety of hormone-related conditions, for example conditions associated with Androgen Decline in Aging Male (ADAM); c) treatment of conditions associated with Androgen Decline in Female (ADIF); d) treatment and/or prevention of chronic muscular wasting; and/or e) decreasing the incidence of, halting or causing a regression of prostate cancer.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857–75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208–18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199–205 (1993) ("Sundaram")). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although concern over sexually transmitted diseases has made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices including IUDs and cervical caps as well as more permanent chemical treatments such as birth control pills and subcutaneous implants. However, to date, the only options available for men include the use of condoms and vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long-term methods which require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320–28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods And Regulation of Male Fertility, "Contraceptive Efficacy of Testosterone-Induced Azoospermia and Oligospermia in Normal Men," Fertility and Sterility 65:821–29 (1996)).

A variety of testosterone esters have been developed which are more slowly absorbed after intramuscular injection and thus result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626–36 (1996)).

Steroidal ligands which bind the AR and act as androgens (e.g. testosterone enanthate) or as antiandrogens (e.g. cyproterone acetate) have been known for many years and are used clinically (Wu 1988). Although nonsteroidal antiandrogens are in clinical use for hormone-dependent prostate cancer, nonsteroidal androgens have not been reported. For this reason, research on male contraceptives has focused solely on steroidal compounds.

Prostate cancer is one of the most frequently occurring cancers among men in the United States, with hundreds of thousands of new cases diagnosed each year. Unfortunately, over sixty percent of newly diagnosed cases of prostate cancer are found to be pathologically advanced, with no cure and a dismal prognosis. One approach to this problem is to find prostate cancer earlier through screening programs and thereby reduce the number of advanced prostate cancer patients. Another strategy, however, is to develop drugs to prevent prostate cancer. One third of all men over 50 years of age have a latent form of prostate cancer that may be activated into the life-threatening clinical prostate cancer form. The frequency of latent prostatic tumors has been shown to increase substantially with each decade of life from the 50s (5.3–14%) to the 90s (40–80%). The number of people with latent prostate cancer is the same across all cultures, ethnic groups, and races, yet the frequency of clinically aggressive cancer is markedly different. This suggests that environmental factors may play a role in activating latent prostate cancer. Thus, the development of treatment and preventative strategies against prostate cancer may have the greatest overall impact both medically and economically against prostate cancer.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the lifecycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

Androgen decline in the aging male (ADAM) refers to a progressive decrease in androgen production, common in males after middle age. The syndrome is characterized by alterations in the physical and intellectual domains that correlate with and can be corrected by manipulation of the androgen milieu. ADAM is characterized biochemically by a decrease not only in serum androgen, but also in other hormones, such as growth hormone, melatonin and dehydroepiandrosterone. Clinical manifestations include fatigue, depression, decreased libido, sexual dysfunction, erectile dysfunction, hypogonadism, osteoporosis, hair loss, obesity, sarcopenia, osteopenia, benign prostate hyperplasia, anemia, alterations in mood and cognition and prostate cancer.

Androgen Deficiency in Female (ADIF) refers to a variety of hormone-related conditions including, common in females after middle agest. The syndrome is characterized by sexual dysfunction, decreased sexual libido, hypogonadism, sarcopenia, osteopenia, osteoporosis, alterations in cognition and mood, anemia, depression, anemia, hair loss, obesity, endometriosis, breast cancer, uterine cancer and ovarian cancer.

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle. The loss of muscle mass that occurs during muscle wasting can be characterized by a muscle protein breakdown or degradation. Protein degradation occurs because of an unusually high rate of protein degradation, an unusually low rate of protein synthesis, or a combination of both. Protein degradation, whether caused by a high degree of protein degradation or a low degree of protein synthesis, leads to a decrease in muscle mass and to muscle wasting. Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Emphysema, Osteomalacia, HIV Infection, AIDS, and Cardiomyopathy, In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism. Muscle wasting, if left unabated, can have dire health consequences. For example, the changes that occur during muscle wasting can lead to a weakened physical state that is detrimental to an individual's health, resulting in increased susceptibility to infection, poor performance status and susceptibility to injury.

New innovative approaches are urgently needed at both the basic science and clinical levels to develop compounds which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; and/or e) decreasing the incidence of, halting or causing a regression of prostate cancer.

SUMMARY OF THE INVENTION

In one embodiment, this invention provides pharmaceutical compositions and formulations comprising a novel class of androgen receptor targeting agents (ARTA) which demonstrate androgenic and anabolic activity of a nonsteroidal ligand for the androgen receptor. The agents define a new subclass of compounds which are selective androgen receptor modulators (SARM) which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; and/or e) decreasing the incidence of, halting or causing a regression of prostate cancer. The present invention provides pharmaceutical compositions comprising the selective androgen receptor modulator compounds, together with pharmaceutically acceptable excipients.

Thus, in one embodiment, the present invention provides a pharmaceutical composition comprising a) a selective androgen receptor modulator (SARM) compound having in-vivo androgenic and anabolic activity of a nonsteroidal ligand for the androgen receptor, the compound represented by the structure of formula I, or its analog, isomer, metabolite, derivative, pharmaceutically acceptable salt, pharmaceutical product, N-oxide, hydrate or any combination thereof; and b) a pharmaceutically acceptable carrier or diluent.

I wherein
X is O, $CH_2$, NH, Se, PR, NO or NR;
T is OH, OR, —$NHCOCH_3$, or NHCOR;

Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ling system represented by structure A, B or C:

A

B

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$.

In one embodiment, X in compound I is O. In another embodiment, Z in compound I is $NO_2$. In another embodiment, Z in compound I is CN. In another embodiment, Y in compound I is $CF_3$. In another embodiment, Q in compound I is $NHCOCH_3$. In another embodiment, Q in compound I is F. In another embodiment, T in compound I is OH. In another embodiment, $R_1$ in compound I is $CH_3$. In another embodiment, Q in compound I is in the para position. In another embodiment, Z in compound I is in the para position. In another embodiment, Y in compound I is in the meta position.

In another embodiment, the SARM compound is represented by the structure of formula II, or its analog, isomer, metabolite, derivative, pharmaceutically acceptable salt, pharmaceutical product, N-oxide, hydrate or any combination thereof.

II wherein the substituents Q, Z and Y are as defined above for the compound of formula I.

In another embodiment, the SARM compound is represented by the structure of formula III, or its analog, isomer, metabolite, derivative, pharmaceutically acceptable salt, pharmaceutical product, N-oxide, hydrate or any combination thereof.

III

In another embodiment, the SARM compound is represented by the structure of formula IV, or its analog, isomer, metabolite, derivative, pharmaceutically acceptable salt, pharmaceutical product, N-oxide, hydrate or any combination thereof.

IV

In one embodiment, the carrier or diluent is a gum, a starch, a sugar, a cellulosic material, an acrylate, calcium carbonate, magnesium oxide, talc, or mixtures thereof. In another embodiment, the carrier is lactose monohydrate, microcrystalline cellulose, or a mixture thereof.

In one embodiment, the composition further comprises a lubricant. In another embodiment, the lubricant is magnesium stearate. In another embodiment, the composition further comprises a flow aid. In another embodiment, the flow aid is colloidal silicon dioxide. In another embodiment, the composition further comprises one or more additives selected from a binder, a disintegrant, a buffer, a protease inhibitor, a surfactant, a solubilizing agent, a plasticizer, an emulsifier, a stabilizing agent, a viscosity increasing agent, a sweetner, a film forming agent or any combination thereof.

In one embodiment, the composition is in the form of a capsule. In accordance with this embodiment, the composition further comprises a hard gelatin capsule. In another embodiment, the composition is in the form of a pellet, a tablet, a solution, a suspension, a dispersion, an emulsion, an elixir, a gel, an ointment, a cream, a powder, or a suppository. In one embodiment, the composition is in a liquid dosage form. In another embodiment, the composition is in a solid dosage form.

In one embodiment, the composition is in a form suitable for oral, intravenous, intraarterial, intramuscular, subcutaneous, parenteral, transmucosal, transdermal, intravaginal or topical administration. In another embodiment, the composition is a controlled release composition. In another embodiment, the composition is an immediate release composition.

Further, in one embodiment, the present invention provides a pharmaceutical composition comprising a) a selective androgen receptor modulator (SARM) compound having in-vivo androgenic and anabolic activity of a nonsteroidal ligand for the androgen receptor, said compound represented by the structure of any of formulas I–IV, or its analog, isomer, metabolite, derivative, pharmaceutically acceptable salt, pharmaceutical product, N-oxide, hydrate or any combination thereof; b) a pharmaceutically acceptable carrier or diluent; c) a flow-aid; and d) a lubricant.

Further, in another embodiment, the present invention provides a pharmaceutical composition comprising a) a selective androgen receptor modulator (SARM) compound having in-vivo androgenic and anabolic activity of a nonsteroidal ligand for the androgen receptor, said compound represented by the structure of any of formulas I–IV, or its analog, isomer, metabolite, derivative, pharmaceutically acceptable salt, pharmaceutical product, N-oxide, hydrate or any combination thereof; b) lactose monohydrate; c) microcrystalline cellulose; d) magnesium stearate; and e) colloidal silicon dioxide.

The novel selective androgen receptor modulator compounds of the present invention, either alone or as a pharmaceutical composition, are useful for a) male contraception; b) treatment of a variety of hormone-related conditions, for example conditions associated with ADAM, such as fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; and/or e) decreasing the incidence of, halting or causing a regression of prostate cancer.

The compositions comprising the selective androgen receptor modulator compounds of the present invention offer a significant advance over steroidal androgen treatment because the selective androgen receptor modulator compounds of the present invention have been shown in-vivo to have an androgenic and anabolic activity of a nonsteroidal ligand for the androgen receptor. Thus, the selective androgen receptor modulator compounds have an androgenic and anabolic activity of a nonsteroidal ligand for the androgen receptor and will not be accompanied by serious side effects, inconvenient modes of administration, or high costs and still have the advantages of oral bioavailability, lack of cross-reactivity with other steroid receptors, and long biological half-lives.

BRIEF DESCRIPTION OF THE FIGURES

The present invention will be understood and appreciated more fully from the following detailed description taken in conduction with the appended figures in which.

DETAILED DESCRIPTION OF THE INVENTION

The present invention relates to a novel class of androgen receptor targeting agents (ARTA) which demonstrate androgenic and anabolic activity of a nonsteroidal ligand for the androgen receptor. The agents define a new subclass of compounds which are selective androgen receptor modulators (SARM) which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; and/or e) decreasing the incidence of, halting or causing a regression of prostate cancer. The present invention provides pharmaceutical compositions comprising the selective androgen receptor modulator compounds, together with pharmaceutically acceptable excipients.

Thus, in one embodiment, the present invention provides a pharmaceutical composition comprising a) a selective androgen receptor modulator (SARM) compound having in-vivo androgenic and anabolic activity of a nonsteroidal ligand for the androgen receptor, the compound represented by the structure of formula I, or its analog, isomer, metabolite, derivative, pharmaceutically acceptable salt, pharmaceutical product, N-oxide, hydrate or any combination thereof; and b) a pharmaceutically acceptable carrier or diluent.

I wherein

X is O, CH$_2$, NH, Se, PR, NO or NR;

T is OH, OR, —NHCOCH$_3$, or NHCOR;

Z is NO$_2$, CN, COOH, COR, NHCOR or CONHR;

Y is CF$_3$, F, I, Br, Cl, CN, CR$_3$ or SnR$_3$;

Q is alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

A

B

C

R is alkyl, haloalkyl, dihaloalkyl, trihaloalkyl, CH$_2$F, CHF$_2$, CF$_3$, CF$_2$CF$_3$, alkyl, phenyl, halogen, alkenyl or OH; and R$_1$ is CH$_3$, CH$_2$F, CHF$_2$, CF$_3$, CH$_2$CH$_3$, or CF$_2$CF$_3$.

In one embodiment, this invention provides a pharmaceutical composition comprising a selective androgen modulator compound of formula I wherein X is O, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein Z is NO$_2$, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein Z is CN, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein Y is CF$_3$, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein Q is NHCOCH$_3$, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein Q is F, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein T is OH, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein R$_1$ is CH$_3$, or its analog, isomer, metabolite, derivative, pharmaceutically acceptable salt, pharmaceutical product, N-oxide, hydrate or any combination thereof.

In another embodiment, this invention provides a pharmaceutical composition comprising a selective androgen modulator compound of formula I wherein Q is in the para position, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein Z is in the para position, or its analog, isomer, metabolite, derivative, pharmaceutically acceptable salt, pharmaceutical product, N-oxide, hydrate or any combination thereof. In another embodiment, this invention provides a pharmaceutical composition comprising a selective androgen modulator compound of formula I wherein Y is in the meta position, or its analog, isomer, metabolite, derivative, pharmaceutically acceptable salt, pharmaceutical product, N-oxide, hydrate or any combination thereof.

In another embodiment, the SARM compound is represented by the structure of formula II, or its analog, isomer, metabolite, derivative, pharmaceutically acceptable salt, pharmaceutical product, N-oxide, hydrate or any combination thereof.

wherein the substituents Q, Z and Y are as defined above for the compound of formula I.

In another embodiment, the SARM compound is represented by the structure of formula III, or its analog, isomer, metabolite, derivative, pharmaceutically acceptable salt, pharmaceutical product, N-oxide, hydrate or any combination thereof.

In another embodiment, the SARM compound is represented by the structure of formula IV, or its analog, isomer, metabolite, derivative, pharmaceutically acceptable salt, pharmaceutical product, N-oxide, hydrate or any combination thereof.

In one embodiment, this invention provides a pharmaceutical composition comprising an analog of the compound of any of formulas I–IV. In another embodiment, this invention provides a pharmaceutical composition comprising a derivative of the compound of any of formulas I–IV. In another embodiment, this invention provides a pharmaceutical composition comprising an isomer of any of formulas I–IV, for example the S isomer, the R isomer, of a combination thereof. In another embodiment, this invention provides a pharmaceutical composition comprising a metabolite of the compound of any of formulas I–IV. In another embodiment, this invention provides a pharmaceutical composition comprising a pharmaceutically acceptable salt of the compound of any of formulas I–IV. In another embodiment, this invention provides a pharmaceutical composition comprising a pharmaceutical product of the compound of any of formulas I–IV. In another embodiment, this invention provides a pharmaceutical composition comprising a hydrate of the compound of any of formulas I–IV. In another embodiment, this invention provides a pharmaceutical composition comprising an N-oxide of the compound of any of formulas I–IV. In another embodiment, this invention provides a pharmaceutical composition comprising a combination of any of an analog, derivative, metabolite, isomer, pharmaceutically acceptable salt, pharmaceutical product, hydrate or N-oxide of the compound of any of formulas I–IV.

As contemplated herein, the Selective Androgen Modulator (SARM) compounds are the active ingredients in the pharmaceutical compositions provided by the present invention. The SARM compound may be any one of the compounds encompassed by the structures of formulas I–IV. In one embodiment, the pharmaceutical compositions comprise one SARM compound as an active ingredient. In alternative embodiment, the pharmaceutical compositions comprise more than one SARM compound, for example a combination of two, three or more SARM compounds. Further, the active ingredient in the pharmaceutical compositions can be an analog, isomer, metabolite, derivative, pharmaceutically acceptable salt, pharmaceutical product, N-oxide or hydrate, or any combination thereof of the SARM compound.

The substituent R is defined herein as an alkyl, haloalkyl, dihaloalkyl, trihaloalkyl, $CH_2F$, $CHF_2$, $CF_3$, $CF_2CF_3$; aryl, phenyl, halogen, alkenyl, or hydroxyl (OH).

An "alkyl" group refers to a saturated aliphatic hydrocarbon, including straight-chain, branched-chain and cyclic alkyl groups. In one embodiment, the alkyl group has 1–12 carbons. In another embodiment, the alkyl group has 1–7 carbons. In another embodiment, the alkyl group has 1–6 carbons. In another embodiment, the alkyl group has 1–4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond. A halo group refers to F, Cl, Br or I.

An "arylalkyl" group refers to an alkyl bound to an aryl, wherein alkyl and aryl are as defined above. An example of an aralkyl group is a benzyl group.

As contemplated herein, the present invention relates to the use of a SARM compound and/or its analog, derivative, isomer, metabolite, pharmaceutically acceptable salt, pharmaceutical product, hydrate, N-oxide, or combinations thereof. In one embodiment, the invention relates to the use of an analog of the SARM compound. In another embodiment, the invention relates to the use of a derivative of the SARM compound. In another embodiment, the invention relates to the use of an isomer of the SARM compound. In another embodiment, the invention relates to the use of a metabolite of the SARM compound. In another embodiment, the invention relates to the use of a pharmaceutically acceptable salt of the SARM compound. In another embodiment, the invention relates to the use of a pharmaceutical product of the SARM compound. In another embodiment, the invention relates to the use of a hydrate of the SARM compound. In another embodiment, the invention relates to the use of an N-oxide of the SARM compound.

As defined herein, the term "isomer" includes, but is not limited to, optical isomers and analogs, structural isomers and analogs, conformational isomers and analogs, and the like.

In one embodiment, this invention encompasses the use of various optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the SARM compounds. The term "derivatives" includes but is not limited to ether derivatives, acid derivatives, amide derivatives, ester derivatives and the like. In addition, this invention further includes hydrates of the SARM compounds. The term "hydrate" includes but is not limited to hemihydrate, monohydrate, dihydrate, trihydrate and the like.

This invention further includes metabolites of the SARM compounds. The term "metabolite" means any substance produced from another substance by metabolism or a metabolic process.

This invention further includes pharmaceutical products of the SARM compounds. The term "pharmaceutical product" means a composition suitable for pharmaceutical use (pharmaceutical composition), as defined herein.

Pharmaceutical Compositions

As used herein, "pharmaceutical composition" means a "therapeutically effective amount" of the active ingredient, i.e. the SARM compound, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the SARM agent can be administered to a subject by any method known to a person skilled in the art, such as orally, parenterally, paracancerally, transmucosally, transdermally, intramuscularly, intravenously, intradermally, subcutaneously, intraperitonealy, intraventricularly, intracranially, intravaginally by inhalation or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to the SARM active compound and the inert carrier or diluent, a hard gelatin capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time. In a further embodiment, the pharmaceutical compositions are administered intravaginally.

In another embodiment, the active compound can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid).

As used herein "pharmaceutically acceptable carriers or diluents" are well known to those skilled in the art. The carrier or diluent may be a solid carrier or diluent for solid formuations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g.

polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleums, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents(e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115–138 (1984). Other controlled release systems are discussed in the review by Langer (Science 249:1527–1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can-be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

Biological Activity of Selective Androgen Modulator Compounds

The pharmaceutical compositions provided herein comprise a new subclass of compounds which are selective androgen receptor modulators (SARM) which are useful for oral testosterone replacement therapy which have an unexpected in-vivo activity for an androgenic and anabolic activity of a nonsteroidal ligand for the androgen receptor. Further, appropriately substituted compounds are effective to treat prostate cancer and useful for imaging of prostate cancer. The SARM compounds demonstrate an in-vivo androgenic and anabolic activity of a nonsteroidal ligand for the androgen receptor.

As contemplated herein, the appropriately substituted SARM compounds of the present invention are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; and/or e) decreasing the incidence of, halting or causing a regression of prostate cancer.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration.

The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction). As a result, substances can be made which bind receptors and activate them (called receptor agonists) or inactivate them (called receptor antagonists). Examples of non-steroidal agonist are described in PCT International Patent Application Number PCT/US98/11020, International filing date May 28, 1998.

In one embodiment, the present invention is directed to selective androgen receptor modulator compounds which are agonist compounds. Thus, in one embodiment, the SARM compounds of the present invention are useful in binding to and activating steroidal hormone receptors. In one embodiment, the agonist compound of the present invention is an agonist which binds the androgen receptor. In another embodiment, the compound has high affinity for the androgen receptor. In another embodiment, the agonist compound also has anabolic activity. In another embodiment, the present invention provides selective androgen modulator compounds which have agonistic and anabolic activity of a nonsteroidal compound for the androgen receptor.

In yet another embodiment, the SARM compounds of the present invention can be classified as partial AR agonist/antagonists. The SARMs are AR agonists in some tissues, and cause increased transcription of AR-responsive genes (e.g. muscle anabolic effect). In other tissues, these compounds serve as inhibitors at the AR to prevent agonistic effects of the native androgens.

Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds to inhibit the growth of AR containing tissue.

The compounds of the present invention bind either reversibly or irreversibly to an androgen receptor. In one embodiment, the androgen receptor is an androgen receptor of a mammal. In another embodiment, the androgen receptor is an androgen receptor of a human. In one embodiment, the SARM compounds bind reversibly to the androgen receptor of a mammal, for example a human. Reversible binding of a compound to a receptor means that a compound can detach from the receptor after binding.

In another embodiment, the SARM compounds bind irreversibly to the androgen receptor of a mammal, for example a human. Thus, in one embodiment, the compounds of the present invention may contain a functional group (e.g. affinity label) that allows alkylation of the androgen receptor (i.e. covalent bond formation). Thus, in this case, the compounds are alkylating agents which bind irreversibly to the receptor and, accordingly, cannot be displaced by a steroid, such as the endogenous ligands DHT and testosterone. An "alkylating agent" is defined herein as an agent which alkylates (forms a covalent bond) with a cellular component, such as DNA, RNA or enzyme. It is a highly reactive chemical that introduces alkyl radicals into biologically active molecules and thereby prevents their proper functioning. The alkylating moiety is an electrophilic group that interacts with nucleophilic moieties in cellular components.

As defined herein, "contacting" means that the SARM compound of the present invention is introduced into a sample containing the enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in vivo.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

The term "libido, as used herein, means sexual desire.

The term "erectile", as used herein, means capable of being erected. An erectile tissue is a tissue, which is capable of being greatly dilated and made rigid by the distension of the numerous blood vessels which it contains.

"Hypogonadism" is a condition resulting from or characterised by abnormally decreased functional activity of the gonads, with retardation of growth and sexual development. "Osteopenia" refers to decreased calcification or density of bone. This is a term which encompasses all skeletal systems in which such a condition is noted.

"Osteoporosis" refers to a thinning of the bones with reduction in bone mass due to depletion of calcium and bone protein. Osteoporosis predisposes a person to fractures, which are often slow to heal and heal poorly. Unchecked osteoporosis can lead to changes in posture, physical abnormality, and decreased mobility.

"BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

"Cognition" refers to the process of knowing, specifically the process of being aware, knowing, thinking, learning and judging. Cognition is related to the fields of psychology, linguistics, computer science, neuroscience, mathematics, ethology and philosophy. The term "mood" refers to a temper or state of the mind. As contemplated herein, alterations means any change for the positive or negative, in cognition and/or mood.

The term "depression" refers to an illness that involves the body, mood and thoughts, that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

The term "hair loss", medically known as alopecia, refers to baldness as in the very common type of male-pattern baldness. Baldness typically begins with patch hair loss on the scalp and sometimes progresses to complete baldness and even loss of body hair. Hair loss affects both males and females.

"Anemia" refers to the condition of having less than the normal number of red blood cells or less than the normal quantity of hemoglobin in the blood. The oxygen-carrying capacity of the blood is, therefore, decreased. Persons with anemia may feel tired and fatigue easily, appear pale, develop palpitations and become usually short of breath. Anemia is caused by four basic factors: a) hemorrhage (bleeding); b) hemolysis (excessive destruction of red blood cells); c) underproduction of red blood cells; and d) not enough normal hemoglobin. There are many forms of anemia, including aplastic anemia, benzene poisoning, Fanconi anemia, hemolytic disease of the newborn, hereditary spherocytosis, iron deficiency anemia, osteopetrosis, pernicious anemia, sickle cell disease, thalassemia, myelodysplastic syndrome, and a variety of bone marrow diseases. As contemplated herein, the SARM compounds of the present invention are useful in preventing and/or treating any one or more of the above-listed forms of anemia.

"Obesity" refers to the state of being well above one's normal weight. Traditionally, a person is considered to be obese if they are more than 20 percent over their ideal weight. Obesity has been more precisely defined by the National Institute of Health (NIH) as a Body to Mass Index (BMI) of 30 or above. Obesity is often multifactorial, based on both genetic and behavioral factors. Overweight due to obesity is a significant contributor to health problems. It increases the risk of developing a number of diseases including: Type 2 (adult-onset) diabetes; high blood pressure (hypertension); stroke (cerebrovascular accident or CVA); heart attack (myocardial infarction or MI); heart failure (congestive heart failure); cancer (certain forms such as cancer of the prostate and cancer of the colon and rectum); gallstones and gallbladder disease (cholecystitis); Gout and gouty arthritis; osteoarthritis (degenerative arthritis) of the knees, hips, and the lower back; sleep apnea (failure to breath normally during sleep, lowering blood oxygen); and Pickwickian syndrome (obesity, red face, underventilation and drowsiness). As contemplated herein, the term "obesity" includes any one of the above-listed obesity-related conditions and diseases. Thus the SARM compounds of the present invention are useful in preventing and/or treating obesity and any one or more of the above-listed obesity-related conditions and diseases.

"Prostate cancer" is one of the most frequently occurring cancers among men in the United States, with hundreds of thousands of new cases diagnosed each year. Over sixty percent of newly diagnosed cases of prostate cancer are found to be pathologically advanced, with no cure and a dismal prognosis. One third of all men over 50 years of age have a latent form of prostate cancer that may be activated into the life-threatening clinical prostate cancer form. The frequency of latent prostatic tumors has been shown to increase substantially with each decade of life from the 50s (5.3–14%) to the 90s (40–80%). The number of people with latent prostate cancer is the same across all cultures, ethnic groups, and races, yet the frequency of clinically aggressive cancer is markedly different. This suggests that environmental factors may play a role in activating latent prostate cancer.

In one embodiment, the pharmaceutical compositions of the present invention comprise administering a SARM compound as the sole active ingredient. However, also encompassed within the scope of the present invention are methods for hormone therapy, for treating prostate cancer, for delaying the progression of prostate cancer, and for preventing and/or treating the recurrence of prostate cancer, which comprise administering the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMS.

Thus, in one embodiment, the present invention provides compositions and pharmaceutical compositions comprising a selective androgen receptor modulator compound, in combination with an LHRH analog. In another embodiment, the present invention provides compositions and pharmaceutical compositions comprising a selective androgen receptor modulator compound, in combination with a reversible antiandrogen. In another embodiment, the present invention provides compositions and pharmaceutical compositions comprising a selective androgen receptor modulator compound, in combination with an antiestrogen. In another embodiment, the present invention provides compositions and pharmaceutical compositions comprising a selective androgen receptor modulator compound, in combination with an anticancer drug. In another embodiment, the present invention provides compositions and pharmaceutical compositions comprising a selective androgen receptor modulator compound, in combination with a 5-alpha reductase inhibitor. In another embodiment, the present invention provides compositions and pharmaceutical compositions comprising a selective androgen receptor modulator compound, in combination with an aromatase inhibitor. In another embodiment, the present invention provides compositions and pharmaceutical compositions comprising a selective androgen receptor modulator compound, in combination with a progestin. In another embodiment, the present invention provides compositions and pharmaceutical compositions comprising a selective androgen receptor modulator compound, in combination with an agent acting through other nuclear hormone receptors. In another embodiment, the present invention provides compositions and pharmaceutical compositions comprising a selective androgen receptor modulator compound, in combination with a selective estrogen receptor modulators (SERM). In another embodiment, the present invention provides compositions and pharmaceutical compositions comprising a selective androgen receptor modulator compound, in combination with progesterone. In another embodiment, the present invention provides compositions and pharmaceutical compositions comprising a selective androgen receptor modulator compound, in combination with estrogen. In another embodiment, the present invention provides compositions and pharmaceutical compositions comprising a selective androgen receptor modulator compound, in combination with PDE5 inhibitors. In another embodiment, the present invention provides compositions and pharmaceutical compositions comprising a selective androgen receptor modulator compound, in combination with apomorphine. In another embodiment, the present invention provides compositions and pharmaceutical compositions comprising a selective androgen receptor modulator compound, in combination with a bisphosphonate. In another embodiment, the present invention provides compositions and pharmaceutical compositions comprising a selective androgen receptor modulator compound, in combination with one or more additional SARMS.

The following examples are presented in order to more fully illustrate the preferred embodiments of the invention. They should in no way be construed, however, as limiting the broad scope of the invention.

Experimental Details Section

Example 1

Pharmaceutical Compositions Comprising Compound III

The active ingredient is Compound III (>99.9% pure S-isomer). The inactive ingredients are lactose monohydrate, lactose fast-flo 316, Avicel PH102 (microcrystalline cellulose), magnesium stearate and colloidal silicon dioxide. The blended active and inactive ingredients are filled into white opaque hard gelatin capsules (size one).

Quantitative Composition

TABLE 1

1 mg FORMULATION

| Ingredient: | Manufacturer: | Excipient Purpose: | Weight/Count Per dosage unit: | Weight/Count Per Batch*: |
|---|---|---|---|---|
| Compound III | ChemSyn Laboratories | Active | 1.00 mg | 0.500 g |
| Lactose Monohydrate, NF (#310 Regular) | Foremost | Diluent/Filler | 80.00 mg | 40.000 g |
| Lactose Monohydrate, NF (#316 Fast-Flo Modified, Spray-Dried) | Foremost | Filler/Flow-Aid | 196.45 mg | 98.225 g |
| Microcrystalline Cellulose, NF (Avicel PH102) | FMC | Filler/Disintegrant | 30.00 mg | 15.000 g |
| Silicon Dioxide, Colloidal, USP/NF (Cab-O-Sil M-5P) | Cabot | Flow-Aid | 1.00 mg | 0.500 g |
| Magnesium Stearate, NF HyQual | Mallinckrodt | Lubricant | 1.55 mg | 0.775 g |
| Capsule, Hard Gelatin Size 1, White Opaque | Capsugel | Capsule | 1 (Count) | 500 (Count) |

*Batch size based on 500 capsules but may change depending on requirements

TABLE 2

0.1 mg FORMULATION

| Ingredient: | Manufacturer: | Excipient Purpose: | Weight/Count Per dosage unit: | Weight/Count Per Batch*: |
|---|---|---|---|---|
| Compound III | ChemSyn Laboratories | Active | 0.10 mg | 0.050 g |
| Lactose Monohydrate, NF (#310 Regular) | Foremost | Diluent/Filler | 80.00 mg | 40.000 g |
| Lactose Monohydrate, NF (#316 Fast-Flo Modified, Spray-Dried) | Foremost | Filler/Flow-Aid | 197.35 mg | 98.675 g |
| Microcrystalline Cellulose, NF (Avicel PH102) | FMC | Filler/Disintegrant | 30.00 mg | 15.000 g |
| Silicon Dioxide, Colloidal, USP/NF (Cab-O-Sil M-5P) | Cabot | Flow-Aid | 1.00 mg | 0.500 g |
| Magnesium Stearate, NF HyQual | Mallinckrodt | Lubricant | 1.55 mg | 0.775 g |
| Capsule, Hard Gelatin Size 1, White Opaque | Capsugel | Capsule | 1 (Count) | 500 (Count) |

*Batch size based on 500 capsules but may change depending on requirements

Specifications and Analytical Methods for Inactive Compounds

All active ingredients included in the formulation have monographs that denote full compendial testing per Standard Operating Procedure of the manufacturer.

Method of Manufacturing

Figure 1:
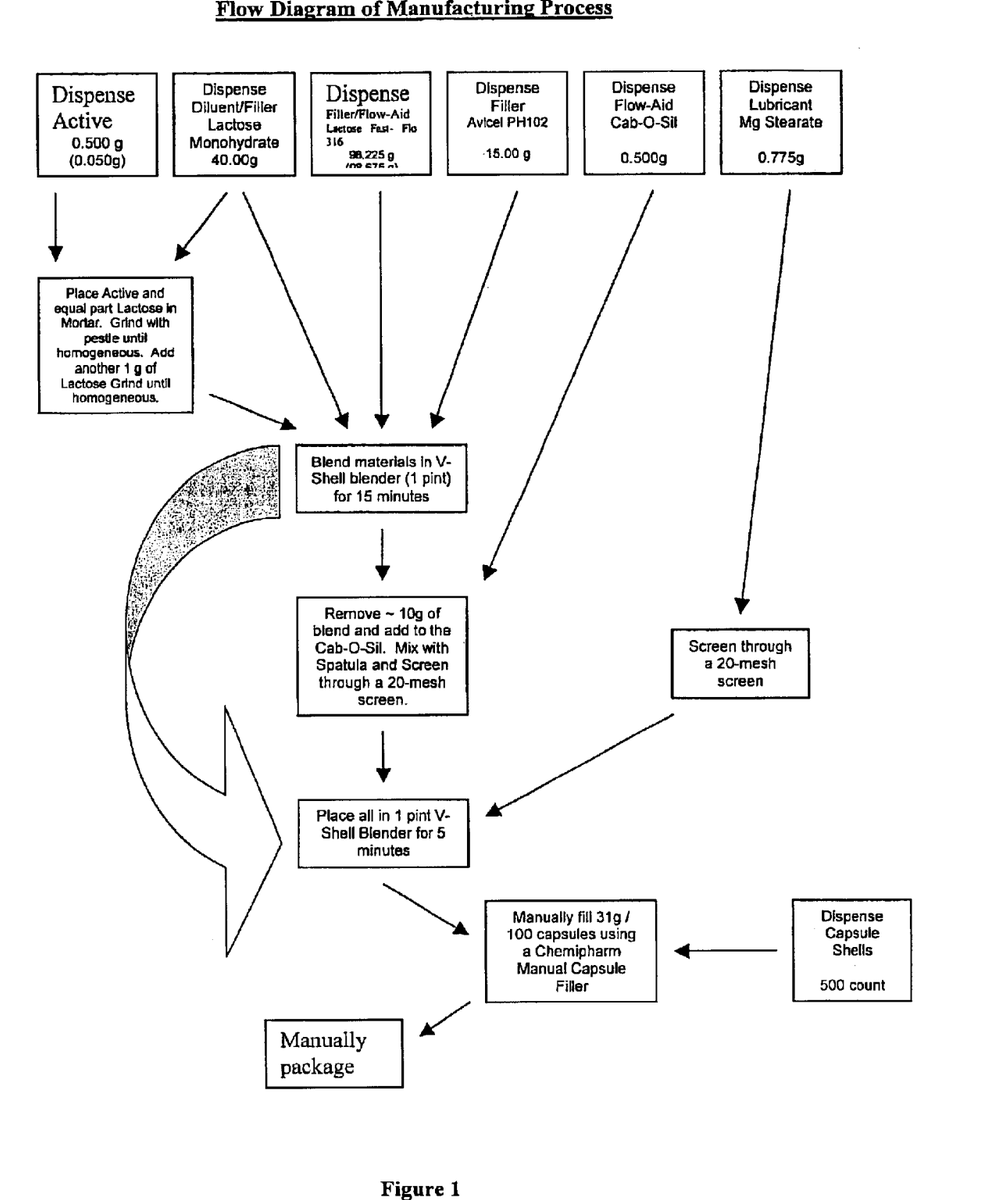
FIG. 1: a flow diagram illustrating the manufacturing process of the pharmaceutical compositions of the present invention.

Capsules of Compound III are manufactured in accordance with the flow chart depicted in FIG. 1, using the formulations as set forth in Table 1 (1 mg formulation) and Table 2 (0.1 mg formulation).

For 1 mg Compound III capsules: the indicated amount of active and inactive ingredients are dispensed. 0.5 grams of Compound III (active pharmaceutical ingredient, API) are diluted by placing API and an equal part of lactose monohydrate (0.5 grams) in mortar. The mixture is ground with a pestle until homogenous. The mixture is diluted again by adding one additional gram of lactose monohydrate to the mixture and grinding until homogenous. The diluted active: lactose monohydrate mixture is blended with 38.5 grams of lactose monohydrate, 98.225 grams of lactose fast-flo, and 15 grams of Avicel PH102 in a one pint V-shell blender for 15 minutes. Approximately 10 grams of the blend is removed and added to 0.5 grams of Cab-O-Sil. The mixture is mixed with a spatula and screened through a 20-mesh screen. 0.775 grams of magnesium stearate are independently screened through a 20-mesh screen. The screened ingredients (10 grams of initial blend with Cab-O-Sil, and magnesium stearate) are added to the remainder of the initial blend in the one pint V-shell blender. All ingredients are blended together in a V-shell blender for five minutes. Capsule shells (500 count) are dispensed into a Chemipharm Manual Capsule Filler. 31 grams of blended mixture are manually filled into 100 capsules using the Chemipharm Manual Capsule Filler. The capsules are manually packaged and labeled. Each capsule contains 1 milligram of active and 309 milligrams of inactive ingredients.

For 0.1 mg Compound III capsules: the same Method of Manufacturing is used, the amounts of GTx-007 API and inactive ingredients are adjusted accordingly (Table 2 and flow diagram in FIG. 1).

It will be appreciated by a person skilled in the art that the present invention is not limited by what has been particularly shown and described hereinabove. Rather, the scope of the invention is defined by the claims that follow:

What is claimed is:

1. A pharmaceutical composition comprising:

a selective androgen receptor modulator (SARM) compound having in-vivo androgenic and anabolic activity of a nonsteroidal ligand for the androgen receptor, said compound represented by the structure of formula I:

wherein
X is O, $CH_2$, NH, Se, PR, NO or NR;
T is OH, OR, —$NHCOCH_3$, or NHCOR;
Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$;
and a pharmaceutically acceptable carrier or diluent.

2. The composition according to claim 1, comprising an analog, isomer, metabolite, derivative, pharmaceutically acceptable salt, pharmaceutical product, N-oxide, hydrate or any combination thereof of the compound of formula I.

3. The composition according to claim 1, wherein X is O.

4. The composition according to claim 1, wherein Z is $NO_2$.

5. The composition according to claim 1, wherein Z is CN.

6. The composition according to claim 1, wherein Y is $CF_3$.

7. The composition according to claim 1, wherein Q is $NHCOCH_3$.

8. The composition according to claim 1, wherein Q is F.

9. The composition according to claim 1, wherein T is OH.

10. The composition according to claim 1, wherein $R_1$ is $CH_3$.

11. The composition according to claim 1, wherein Q is in the para position.

12. The composition according to claim 1, wherein Z is in the para position.

13. The composition according to claim 1, wherein Y is in the meta position.

14. The composition according to claim 1, wherein said selective androgen receptor modulator compound is represented by the structure of formula II:

15. The composition according to claim 1, wherein said selective androgen receptor modulator compound is represented by the structure of formula III:

16. The composition according to claim 1, wherein said selective androgen receptor modulator compound is represented by the structure of formula IV:

17. The composition according to claim 1, wherein said carrier or diluent is a gum, a starch, a sugar, a cellulosic material, an acrylate, calcium carbonate, magnesium oxide, talc, or mixtures thereof.

18. The composition according to claim 1, wherein said carrier or diluent is lactose monohydrate, microcrystalline cellulose, or a mixture thereof.

19. The composition according to claim 1, further comprising a lubricant.

20. The composition of claim 19, wherein said lubricant is magnesium stearate.

21. The composition according to claim 1, further comprising a flow-aid.

22. The composition according to claim 21, wherein said flow aid is colloidal silicon dioxide.

23. The composition according to claim 1, further comprising one or more additives selected from a binder, a disintegrant, a buffer, a protease inhibitor, a surfactant, a solubilizing agent, a plasticizer, an emulsifier, a stabilizing agent, a viscosity increasing agent, a sweetner, a film forming agent, or any combination thereof.

24. The composition according to claim 1, wherein said composition is in the form of a pellet, a tablet, a capsule, a solution, a suspension, a dispersion, an emulsion, an elixir, a gel, an ointment, a cream, a powder or a suppository.

25. The composition according to claim 1, wherein said composition is in the form of a capsule.

26. The composition according to claim 1, wherein said composition is in a form suitable for oral, intravenous, intraarterial, intramuscular, subcutaneous, parenteral, transmucosal, transdermal, intravaginal or topical administration.

27. The composition according to claim 1, wherein said composition is in a form suitable for oral administration.

28. The composition according to claim 1, wherein said composition is a controlled release composition.

29. The composition according to claim 1, wherein said composition is an immediate release composition.

30. The composition according to claim 1, wherein said composition is a liquid dosage form.

31. The composition according to claim 1, wherein said composition is a solid dosage form.

32. A pharmaceutical composition comprising:

a selective androgen receptor modulator (SARM) compound having in-vivo androgenic and anabolic activity of a nonsteroidal ligand for the androgen receptor, said compound represented by the structure of formula I:

I wherein
X is O, $CH_2$, NH, Se, PR, NO or NR;
T is OH, OR, —$NHCOCH_3$, or NHCOR;
Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

A

B

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$;

a pharmaceutically acceptable carrier or diluent;

a flow-aid; and a lubricant.

33. The composition according to claim 32, comprising an analog, isomer, metabolite, derivative, pharmaceutically acceptable salt, pharmaceutical product, N-oxide, hydrate or any combination thereof of the compound of formula I.

34. The composition according to claim 32, wherein X is O.

35. The composition according to claim 32, wherein Z is $NO_2$.

36. The composition according to claim 32, wherein Z is CN.

37. The composition according to claim 32, wherein Y is $CF_3$.

38. The composition according to claim 32, wherein Q is $NHCOCH_3$.

39. The composition according to claim 32, wherein Q is F.

40. The composition according to claim 32, wherein T is OH.

41. The composition according to claim 32, wherein $R_1$ is $CH_3$.

42. The composition according to claim 32, wherein Q is in the para position.

43. The composition according to claim 32, wherein Z is in the para position.

44. The composition according to claim 32, wherein Y is in the meta position.

45. The composition according to claim 32, wherein said selective androgen receptor modulator compound is represented by the structure of formula II:

II

46. The composition according to claim 32, wherein said selective androgen receptor modulator compound is represented by the structure of formula III:

47. The composition according to claim 32, wherein said selective androgen receptor modulator compound is represented by the structure of formula IV:

48. The composition according to claim 32, wherein said carrier or diluent is a gum, a starch, a sugar, a cellulosic material, an acrylate, calcium carbonate, magnesium oxide, talc, or mixtures thereof.

49. The composition according to claim 32, wherein said carrier or diluent is lactose monohydrate, microcrystalline cellulose, or a mixture thereof.

50. The composition of claim 32, wherein said lubricant is magnesium stearate.

51. The composition according to claim 32, wherein said flow aid is colloidal silicon dioxide.

52. The composition according to claim 32, further comprising one or more additives selected from a binder, a disintegrant, a buffer, a protease inhibitor, a surfactant, a solubilizing agent, a plasticizer, an emulsifier, a stabilizing agent, a viscosity increasing agent, a sweetner, a film forming agent, or any combination thereof.

53. The composition according to claim 32, wherein said composition is in the form of a pellet, a tablet, a capsule, a solution, a suspension, a dispersion, an emulsion, an elixir, a gel, an ointment, a cream, a powder or a suppository.

54. The composition according to claim 32, wherein said composition is in the form of a capsule.

55. The composition according to claim 32, wherein said composition is in a form suitable for oral, intravenous, intraarterial, intramuscular, subcutaneous, parenteral, transmucosal, transdermal, intravaginal or topical administration.

56. The composition according to claim 32, wherein said composition is in a form suitable for oral administration.

57. The composition according to claim 32, wherein said composition is a controlled release composition.

58. The composition according to claim 32, wherein said composition is an immediate release composition.

59. The composition according to claim 32, wherein said composition is a liquid dosage form.

60. The composition according to claim 32, wherein said composition is a solid dosage form.

61. A pharmaceutical composition comprising:
a selective androgen receptor modulator (SARM) compound having in-vivo androgenic and anabolic activity of a nonsteroidal ligand for the androgen receptor, said compound represented by the structure of formula I:

wherein
X is O, CH$_2$, NH, Se, PR, NO or NR;
T is OH, OR, —NHCOCH$_3$, or NHCOR;
Z is NO$_2$, CN, COOH, COR, NHCOR or CONHR;
Y is CF$_3$, F, I, Br, Cl, CN, CR$_3$ or SnR$_3$;
Q is alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

A

B

C

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CF$_3$, CH$_2$CH$_3$, or CF$_2$CF$_3$;
lactose monohydrate;
microcrystalline cellulose;
magnesium stearate; and
silicon dioxide.

62. The composition according to claim 61, comprising an analog, isomer, metabolite, derivative, pharmaceutically acceptable salt, pharmaceutical product, N-oxide, hydrate or any combination thereof of the compound of formula I.

63. The composition according to claim 61, wherein X is O.

64. The composition according to claim 61, wherein Z is NO$_2$.

65. The composition according to claim 61, wherein Z is CN.

66. The composition according to claim 61, wherein Y is CF$_3$.

67. The composition according to claim 61, wherein Q is NHCOCH$_3$.

68. The composition according to claim 61, wherein Q is F.

69. The composition according to claim 61, wherein T is OH.

70. The composition according to claim 61, wherein $R_1$ is $CH_3$.

71. The composition according to claim 61, wherein Q is in the para position.

72. The composition according to claim 61, wherein Z is in the para position.

73. The composition according to claim 61, wherein Y is in the meta position.

74. The composition according to claim 32, wherein said selective androgen receptor modulator compound is represented by the structure of formula II:

II

75. The composition according to claim 61, wherein said selective androgen receptor modulator compound is represented by the structure of formula III:

III

76. The composition according to claim 61, wherein said selective androgen receptor modulator compound is represented by the structure of formula IV:

IV

77. The composition according to claim 61, further comprising one or more additives selected from a binder, a disintegrant, a buffer, a protease inhibitor, a surfactant, a solubilizing agent, a plasticizer, an emulsifier, a stabilizing agent, a viscosity increasing agent, a sweetner, a film forming agent, or any combination thereof.

78. The composition according to claim 61, wherein said composition is in the form of a pellet, a tablet, a capsule, a solution, a suspension, a dispersion, an emulsion, an elixir, a gel, an ointment, a cream, a powder or a suppository.

79. The composition according to claim 61, wherein said composition is in the form of a capsule.

80. The composition according to claim 61, wherein said composition is in a form suitable for oral, intravenous, intraarterial, intramuscular, subcutaneous, parenteral, transmucosal, transdermal, intravaginal or topical administration.

81. The composition according to claim 61, wherein said composition is in a form suitable for oral administration.

82. The composition according to claim 61, wherein said composition is a controlled release composition.

83. The composition according to claim 61, wherein said composition is an immediate release composition.

84. The composition according to claim 61, wherein said composition is a liquid dosage form.

85. The composition according to claim 32, wherein said composition is a solid dosage form.

* * * * *

UNITED STATES PATENT AND TRADEMARK OFFICE
CERTIFICATE OF CORRECTION

PATENT NO. : 6,838,484 B2
DATED : January 4, 2005
INVENTOR(S) : Dalton, James T.

It is certified that error appears in the above-identified patent and that said Letters Patent is hereby corrected as shown below:

Title page,
Item [75], Inventors, citizenships for "Yali He" and "Donghua Yin" should read
-- (ROC) --

Column 25,
Line 39, please change to:
-- Q is alkyl, halogen, CF3, CN, CR3, SnR3, NR2, --

Signed and Sealed this

Twenty-fourth Day of May, 2005

JON W. DUDAS
*Director of the United States Patent and Trademark Office*